(12) United States Patent
Kappler

(10) Patent No.: US 10,828,472 B2
(45) Date of Patent: Nov. 10, 2020

(54) FASTENER FOR SECURING TUBES TO A SKIN OF AN ANIMAL

(71) Applicant: Shane Kappler, Cambridge, MA (US)

(72) Inventor: Shane Kappler, Cambridge, MA (US)

( * ) Notice: Subject to any disclaimer, the term of this patent is extended or adjusted under 35 U.S.C. 154(b) by 367 days.

(21) Appl. No.: 15/609,335

(22) Filed: May 31, 2017

(65) Prior Publication Data

US 2017/0348515 A1     Dec. 7, 2017

Related U.S. Application Data

(60) Provisional application No. 62/344,046, filed on Jun. 1, 2016.

(51) Int. Cl.
| | | |
|---|---|---|
| *A61M 27/00* | (2006.01) | |
| *A61M 5/158* | (2006.01) | |
| *F16B 5/06* | (2006.01) | |
| *F16B 2/08* | (2006.01) | |

(52) U.S. Cl.
CPC ........... *A61M 27/00* (2013.01); *F16B 5/0685* (2013.01); *A61M 2005/1586* (2013.01); *A61M 2209/088* (2013.01); *F16B 2/08* (2013.01)

(58) Field of Classification Search
CPC .... A61M 2005/1586; A61M 2209/088; A61M 27/00; A61M 2005/1587; A61M 2025/0286; A61M 25/02; A61M 2025/0266; A61M 2025/0273; A61M 2025/024; A61M 2025/0246; A61M 2025/028
See application file for complete search history.

(56) References Cited

U.S. PATENT DOCUMENTS

| | | | | |
|---|---|---|---|---|
| 4,057,066 A | * | 11/1977 | Taylor ................... | A61M 25/02 604/180 |
| 4,417,710 A | * | 11/1983 | Adair ..................... | A61C 19/00 248/205.2 |
| 4,962,757 A | * | 10/1990 | Stefan .................... | A61M 25/02 128/DIG. 26 |
| 4,981,475 A | * | 1/1991 | Haindl .................. | A61M 25/02 604/174 |
| 4,997,421 A | * | 3/1991 | Palsrok .............. | A61M 39/1011 128/DIG. 26 |
| 5,188,609 A | * | 2/1993 | Bayless ................. | A61M 25/02 604/174 |
| 5,352,211 A | * | 10/1994 | Merskelly ............. | A61M 25/02 128/DIG. 26 |
| 5,382,462 A | * | 1/1995 | Pacione ................ | A44B 18/00 428/100 |
| 5,722,959 A | * | 3/1998 | Bierman ............... | A61M 25/02 128/DIG. 26 |

(Continued)

*Primary Examiner* — Adam Marcetich
(74) *Attorney, Agent, or Firm* — Dunlap Bennett & Ludwig, PLLC

(57) ABSTRACT

A chest tube fastener. The chest tube fastener includes a bracket having a base. The base includes an upper surface and a lower surface with a plurality of openings formed therethrough. A handle is secured to a surface and protrudes from the upper surface of the base. The handle includes a first end opposite a second end. The first end and the second end are attached to the surface and a gap is formed in between the surface and the handle. The base is attached to an animal, such as a human and a tube is attached to the handle.

4 Claims, 3 Drawing Sheets

(56) References Cited

U.S. PATENT DOCUMENTS

| | | | | |
|---|---|---|---|---|
| 5,833,666 A * | 11/1998 | Davis | A61M 25/02 604/180 |
| 6,572,588 B1 * | 6/2003 | Bierman | A61M 25/02 128/DIG. 26 |
| 2003/0236555 A1 * | 12/2003 | Thornes | A61B 17/0401 606/232 |
| 2004/0138624 A1 * | 7/2004 | Bierman | A61M 25/02 604/174 |
| 2005/0137496 A1 * | 6/2005 | Walsh | A61M 25/02 600/561 |
| 2006/0025723 A1 * | 2/2006 | Ballarini | A61M 25/02 604/180 |
| 2006/0058738 A1 * | 3/2006 | Ponzi | A61M 25/02 604/180 |
| 2009/0143742 A1 * | 6/2009 | Bracken | A61M 25/02 604/180 |
| 2009/0216115 A1 * | 8/2009 | Seiler | A61B 90/98 600/426 |
| 2009/0326474 A1 * | 12/2009 | Bierman | A61M 5/1418 604/180 |
| 2011/0118670 A1 * | 5/2011 | Kay | A61M 25/02 604/177 |
| 2013/0310754 A1 * | 11/2013 | Kutsch | A61M 25/02 604/180 |
| 2014/0026891 A1 * | 1/2014 | Winthrop | A61M 16/0497 128/207.14 |
| 2015/0083873 A1 * | 3/2015 | Garpow | F16M 13/02 248/205.3 |
| 2015/0297873 A1 * | 10/2015 | Jenkins | A61M 25/02 604/540 |
| 2016/0114134 A1 * | 4/2016 | Yi | A61F 13/0269 604/180 |
| 2018/0229005 A1 * | 8/2018 | Huizenga | A61M 25/02 |

* cited by examiner

FASTENER FOR SECURING TUBES TO A SKIN OF AN ANIMAL

CROSS-REFERENCE TO RELATED APPLICATION

This application claims the benefit of priority of U.S. provisional application No. 62/344,046, filed Jun. 1, 2016, the contents of which are herein incorporated by reference.

BACKGROUND OF THE INVENTION

The present invention relates to attaching tubes to an outer surface of an animal, such as a patient and, more particularly, to a fastener for securing chest tubes to a human body.

Inserting chest tubes is a lifesaving procedure; however, securing them to the body is currently a cumbersome, prolonged and difficult procedure. When placing a chest tube, the field is often bloody and slippery. Securing a chest tube to the body is most often accomplished using needles, suture and tape. These currently employed methods leave the chest tube tenuously attached to the body, often leading to accidental dislodgement. Moreover, current practices expose healthcare workers to needle sticks, take more time when caring for a critically ill patient and are inherently less secure in keeping the tube in position.

As can be seen, there is a need for a fastener for securing chest tubes to an animal.

SUMMARY OF THE INVENTION

In one aspect of the present invention, a chest tube fastener comprises: a base comprising an upper surface opposite a lower surface and a plurality of openings formed therethrough; and a handle secured to a surface and protruding from the upper surface of the base, wherein the handle comprises a first end opposite a second end, wherein the first end and the second end are attached to the surface and a gap is formed in between the surface and the handle.

In another aspect of the present invention, a method of securing a tube to an animal comprises: providing a base comprising a plurality of openings and a tube connector; connecting a tube to the tube connector; and connecting the base to the animal by suturing the base to the animal or stapling the base to the animal through the plurality of openings.

These and other features, aspects and advantages of the present invention will become better understood with reference to the following drawings, description and claims.

DETAILED DESCRIPTION OF THE INVENTION

Figure 1:
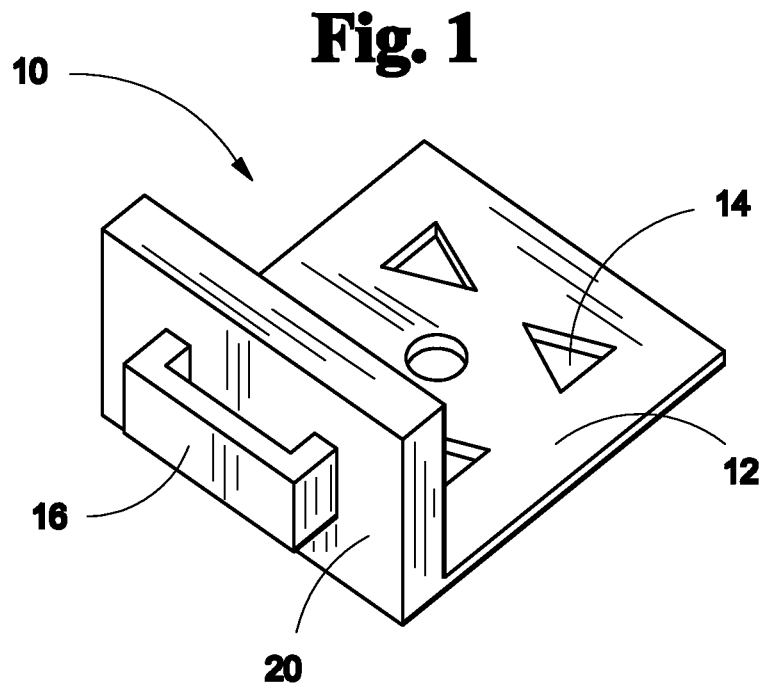
FIG. 1 is a perspective view of an embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Briefly, the invention relates to a medical device comprising a bracket (fastener) adapted for attachment to a body, through which a chest tube is attached to the body of a patient.

The device may be secured to the body through precut holes using staples or sutures, reducing risky needle exposure. The device through its design securely bridges the chest tube's connection to the body increasing the secureness of the position of the tube and reducing movement or dislodgement. Also through its design the fastener decreases tube slippage, movement and/or dislodgement by providing increased traction on the outside of the tube. Finally, with its design it enables attachment of the tube in a fraction of the time compared to conventional methods.

The present invention includes a bracket with a base and attachment handles. The base includes measured pre-cut openings for securing to the body of an animal, such as a human. The present invention further includes a loop connector. The bracket serves as a bridge/securing device/fastener between the tube and body and the loop connector cinches tight around the tube and through the connector handles on the molded bracket. Once the chest tube is inserted into the body, the loop connector encircles the tube, disposed through the connector handle on the bracket and cinching tight around the tube. Afterward, conventional staples or sutures are employed to secure the other part of the bracket to the body through the appropriate pre-cut holes on the bracket.

Referring to FIGS. 1 through 5, the present invention includes a bracket 10 having a base 12. The base 12 includes an upper surface and a lower surface with a plurality of openings 14 formed therethrough. A handle 16 is secured to a surface and protrudes from the upper surface of the base 12. The handle 16 includes a first end opposite a second end. The first end and the second end are attached to the surface and a gap is formed in between the surface and the handle 16. The base 12 is attached to an animal 22, such as a human and a tube 18 is attached to the handle 16.

Figure 2:
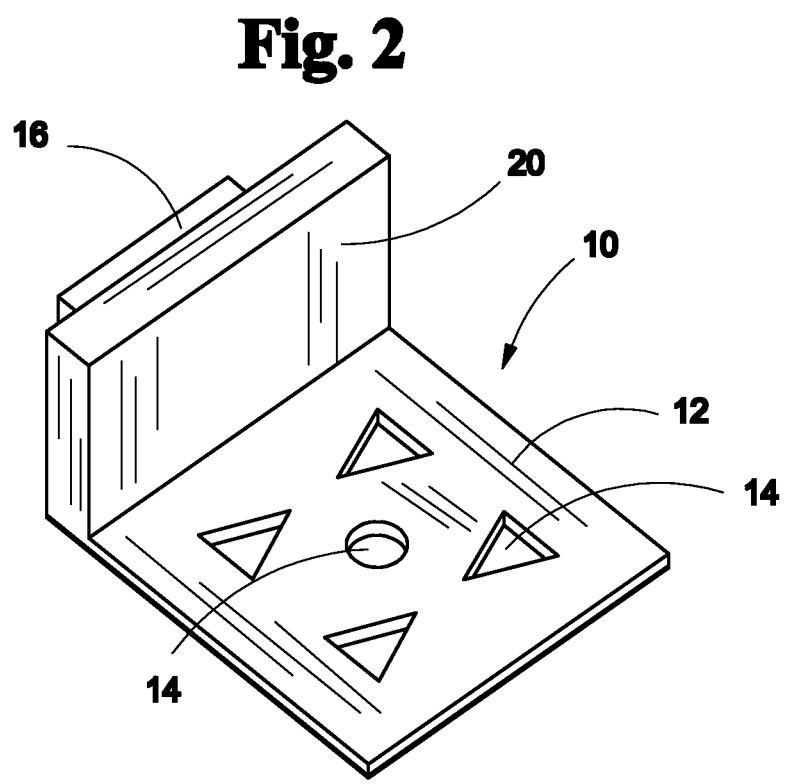
FIG. 2 is a perspective view of an embodiment of the present invention.
Figure 3:
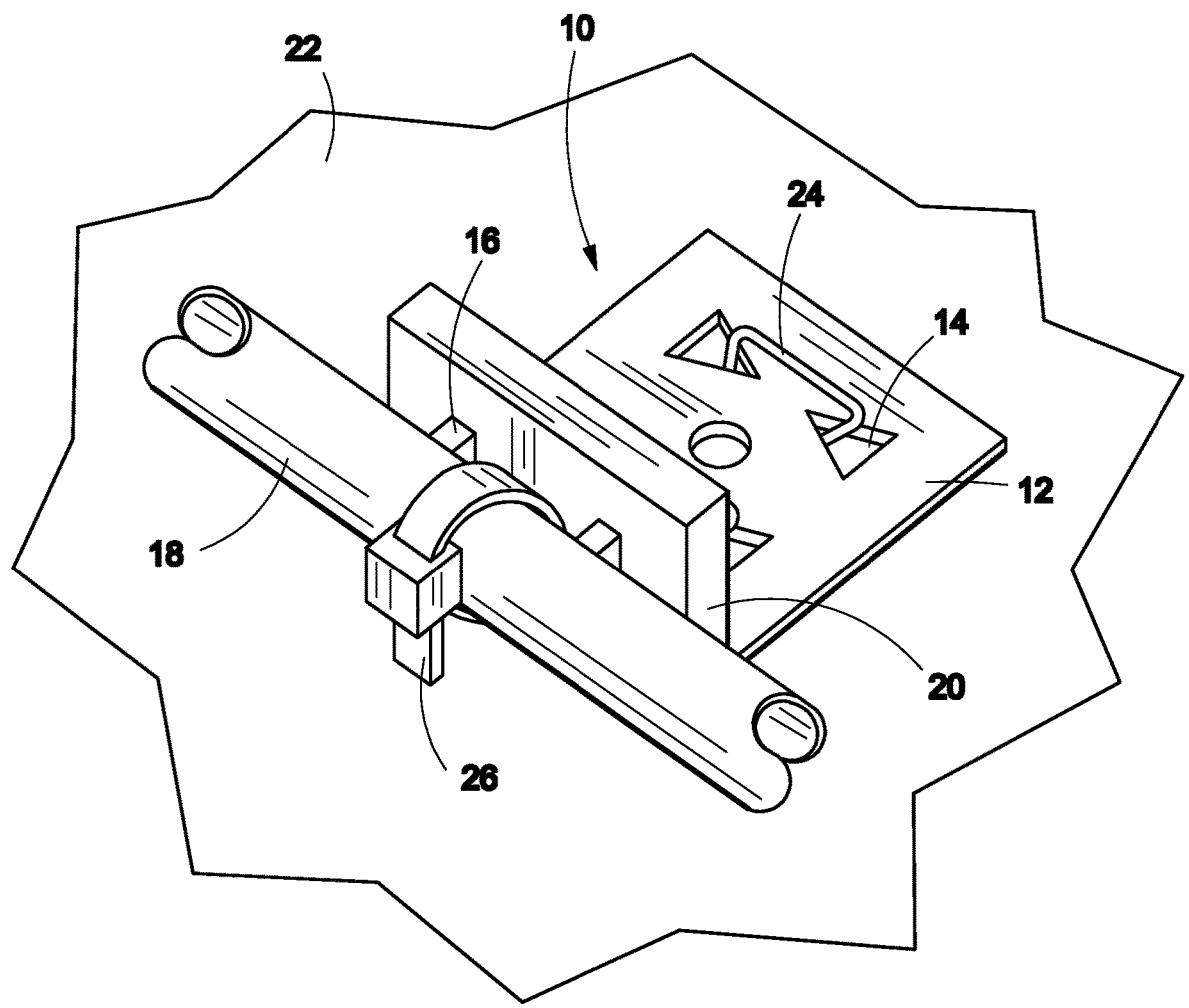
FIG. 3 is a perspective view of an embodiment of the present invention in use.

FIGS. 1 through 3 illustrate a first embodiment of the present invention. The bracket 10 of the present invention includes a base 12 and a sidewall 20. The upper surface and the lower surface of the base 12 may each be planar. The base 12 may include an outer edge. The sidewall 20 extends vertically from the outer edge and thereby may be substantially perpendicular relative to the base 12. The sidewall 20 includes an inner surface facing towards the base 12 and an outer surface facing away from the base 12. The first and second ends of the handle 16 are attached to the outer surface of the sidewall 20.

Figure 4:
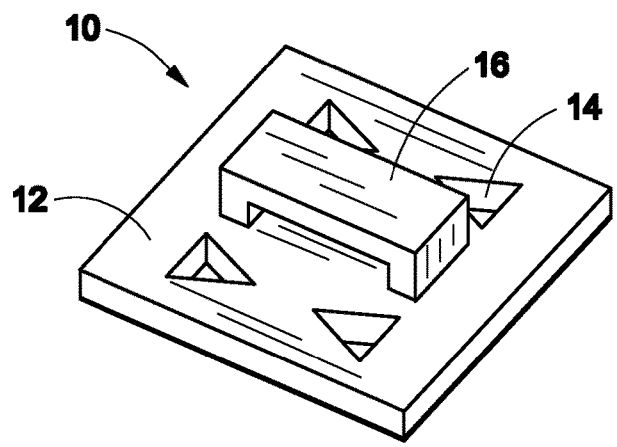
FIG. 4 is a perspective view of an embodiment of the present invention.
Figure 5:
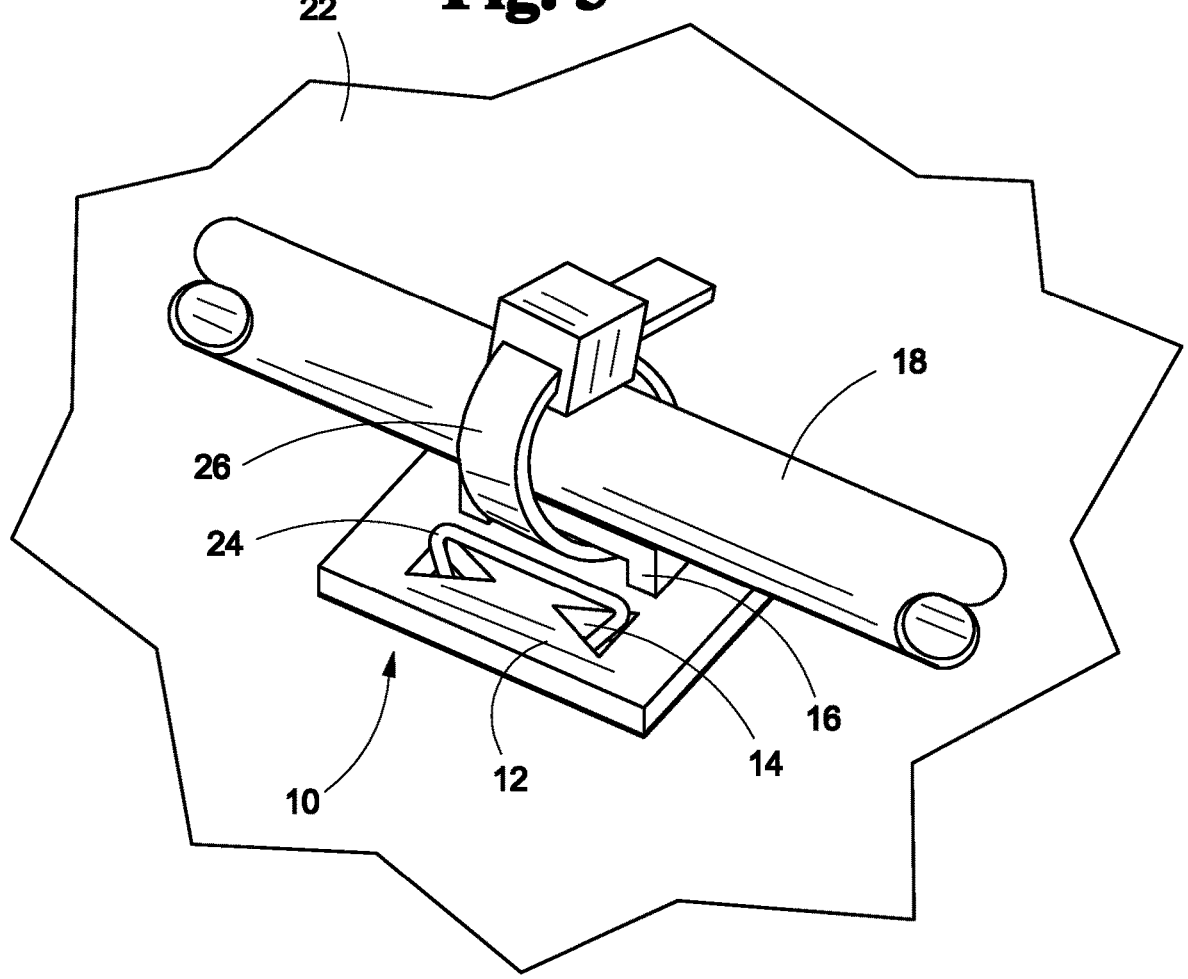
FIG. 5 is a perspective view of an embodiment of the present invention in use.

FIGS. 4 and 5 illustrate a second embodiment of the present invention. The bracket 10 is the base 12. The upper surface and the lower surface of the base 12 may each be planar. The base 12 may include an outer edge forming a square shape. However, the base 12 is not limited to a square shape and may be circular, oval shaped, triangular, rectangular and the like. The first and second ends of the handle 16 are attached to the upper surface of the base 12.

The handle 16 of the present invention may include a central portion, a first side protrusion having the first end and a second side protrusion having the second end. The first side protrusion may be formed by a first bend and the second side protrusion may be formed by a second bend in the same direction as the first bend, forming a U-shape. The U-shaped may be squared at the edges, forming a lower profile. The gap is formed in between the central portion and the surface by the first side protrusion and the second side protrusion elevating the central portion away from the surface.

As mentioned above, the plurality of openings 14 are formed through the base 12. In certain embodiments, the plurality of openings 14 may include at least one pair of openings 14. An inner edge of the base 12 forms the openings 14. In certain embodiments, the inner edge of the base 12 may form a triangular shape, forming a pair of triangular shaped openings 14. The points of the triangular shaped openings 14 may be facing one another. The triangular shaped openings 14 are used to receive and retain staplers 24. In certain embodiments, the present invention may include two pairs of triangular shaped openings 14. In certain embodiments, the plurality of openings 14 may include rounded openings used to receive stitching when the base 12 is sutured to the skin of the animal 22.

In certain embodiments, the tube 18 is attached to the handle 16 by a cable tie 26. The cable tie 26 includes an elongated cord having a head. The elongated cord includes a plurality of teeth that engage with a pawl disposed within the head to form a ratchet so that as the free end of the elongated cord section is pulled the cable tie 26 tightens and does not come undone. The elongated cord is placed through the gap and wraps around the tube 18. The elongated cord is then placed through the head and tightened around the tube 18, securing the tube 18 to the bracket 10. Other connectors may be used to secure the tube 18 to the handle 16, such as straps, buckles and the like.

A method of securing a tube to an animal may include the following steps: providing the bracket mentioned above; connecting a tube to the tube connector; and connecting the base of the bracket to the animal by suturing the base to the animal or stapling the base to the animal through the plurality of openings. When using a chest tube, the chest tube may first be inserted into the animal prior to connecting the tube to the tube connecter. The step of connecting the tube to the tube connector may include the following steps: placing a cable tie through the gap; wrapping the cable tie around the tube; and securing the cable tie to itself.

The bracket and cable tie may be created using a mold. The bracket includes dimensions to be the appropriate size for its use and includes pre-cut holes at specific measurements to fit most medical stapling device sizes and in dimensions appropriate to ensure tight adhesion to the body. The bracket may be attached to the tube through other means and may be interchanged with other tube attachment devices. The attachment of the molded bracket/fastener may be secured to the body through other means such as suturing.

Once the chest tube has been inserted, the plastic loop connector is used to encircle the chest tube. One end is run through the handle on the bracket and cinched until tight around the tube. Now that the bracket is secured to the tube, the other part of the bracket with the precut and measured holes is used to attach to the body using either a medical stapler, suture or string. Additionally, the present invention could be used to secure different catheters or medical devices.

It should be understood, of course, that the foregoing relates to exemplary embodiments of the invention and that modifications may be made without departing from the spirit and scope of the invention as set forth in the following claims.

What is claimed is:

1. A chest tube fastener comprising:
   a base comprising an upper surface opposite a lower surface;
   a handle secured to the upper surface of the base, wherein the handle comprises a central portion, a first side protrusion formed by a first bend and having a first end, a second side protrusion formed by a second bend in a same direction as the first bend and having a second end, the handle having a U-shape, the first end and the second end of the handle attached to the upper surface so that a gap is defined in between the central portion and the upper surface by the first side protrusion and the second side protrusion elevating the central portion away from the upper surface, and
   the base further comprises a first pair of openings disposed on a first side of the handle and a second pair of openings disposed on a second side of the handle opposite the first side,
   wherein a furthest distance between openings of each pair of openings is equal to or less than a furthest distance between the first and second side protrusions, and wherein each pair of openings is dimensioned to receive and retain a medical staple;
   wherein the first pair of openings and the second pair of openings are triangular openings, wherein points of the triangular openings face one another.

2. The chest tube fastener of claim 1, further comprising a connector operable to connect a tube to the handle.

3. The chest tube fastener of claim 2, wherein the connector is a cable tie.

4. A method of securing a tube to an animal comprising:
   providing a chest tube fastener comprising:
      a base comprising an upper surface opposite a lower surface; and
      a handle secured to the upper surface of the base, wherein
         the handle comprises a central portion, a first side protrusion formed by a first bend and having a first end, a second side protrusion formed by a second bend in a same direction as the first bend and having a second end, the handle having a U-shape, the first end and the second end of the handle attached to the upper surface so that a gap is defined in between the central portion and the upper surface by the first side protrusion and the second side protrusion elevating the central portion away from the upper surface, and
      the base further comprises a first pair of openings disposed on a first side of the handle and a second pair of openings disposed on a second side of the handle opposite the first side,
      wherein a furthest distance between openings of each pair of openings is equal to or less than a furthest distance between the first and second side protrusions, and wherein each pair of openings is dimensioned to receive and retain a medical staple;
   placing a cable tie through the gap;
   wrapping the cable tie around a tube;
   securing the cable tie to itself; and
   connecting the base to the animal by suturing the base to the animal or stapling the base to the animal through the first pair of openings and the second pair of openings;
   wherein the first pair of openings and the second pair of openings are triangular openings, wherein points of the triangular openings face one another.

\* \* \* \* \*